United States Patent [19]

Lukens

[11] Patent Number: 4,661,442

[45] Date of Patent: Apr. 28, 1987

[54] PRODUCING LIPID-PROTEIN MEMBRANES FOR CHEMICAL DETECTION

[75] Inventor: Herbert R. Lukens, LaJolla, Calif.

[73] Assignee: IRT Corporation, San Diego, Calif.

[21] Appl. No.: 622,702

[22] Filed: Jun. 20, 1984

[51] Int. Cl.[4] .................. G01N 33/531; G01N 33/544
[52] U.S. Cl. ........................................... 435/4; 435/7; 435/174; 436/501; 436/528; 436/806; 530/812
[58] Field of Search ............... 436/501, 518, 528, 806, 436/807, 149; 260/403; 435/4, 7, 174, 177; 530/810, 812

[56] References Cited

PUBLICATIONS

J. Del Castillo et al., *Science* 153, 185–188, 1966.
M. Mio et al., *Adv. Biosci.* 33, 7–23, 1982.
Y. Rovin in N. Kovarskii (Ed.) *Bisloinye Lipidyne Membr.*, 1983, pp. 3–17, [cited in Chem. Abs. 101, 35254s, 1984].
Janos H. Fendler *C&EN* Jan. 2, 1984, pp. 25–38.
Janos H. Fendler *Membrane Mimetic Chemistry* John Wiley & Sons, New York 1982.

*Primary Examiner*—Sidney Marantz
*Assistant Examiner*—David A. Saunders
*Attorney, Agent, or Firm*—Fitch, Even, Tabin & Flannery

[57] ABSTRACT

Stable lipid-protein membranes are prepared by providing a medium of dissolved and emulsified lipids and dissolved proteins. The medium is applied to an orifice formed in a sheet of material in sufficient volume to provide sufficient lipid and protein to form a membrane across the orifice, which membrane comprises a bimolecular lipid layer with protein molecules interspersed therein. The medium is allowed to dry in the presence of air, and the lipid and protein molecules arrange themselves to form the membrane. The protein is selected to be specifically reactive with a particular chemical substance or a narrow class of chemical substances. When the membrane is exposed to a substance with which the membrane proteins react, a physical characteristic of the membranes is altered. Detection of a change in such membrane characteristic confirms the presence of the substance.

20 Claims, 1 Drawing Figure

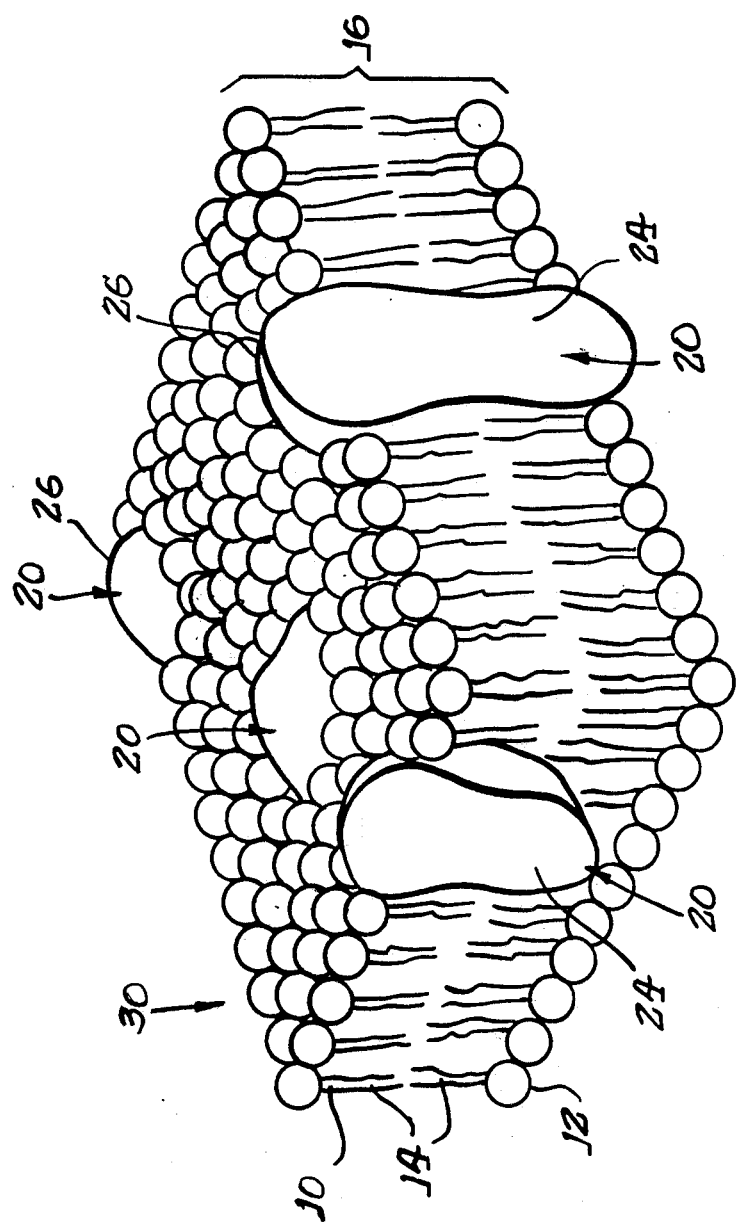

PRODUCING LIPID-PROTEIN MEMBRANES FOR CHEMICAL DETECTION

The present invention is directed to production of lipid-protein membranes which are useful for detecting various chemical substances by nondestructive alteration of one or more characteristics of the membranes.

BACKGROUND OF THE INVENTION

There is a need for rapid, sensitive and specific tests for detecting the presence of various chemical substances in the environment and in biological systems. For example, in warfare, the detection of chemical warfare agents, such as nerve gases, are of critical importance in order to permit personnel to protect themselves against the same. It would be helpful, therefore, if military personnel could carry with them devices which would almost immediately detect trace amounts of chemical warfare substances in the air. Likewise, simple test kits which would immediately and specifically detect the presence of substances in biological samples, such as blood samples, would permit more immediate and precise treatment of various pathogenic conditions.

The present invention utilizes lipid-protein membranes which mimic biological membranes as a means of chemical substance detection. Biomembranes in nature organize living matter by separating cells and cell components from their environment. They consist mostly of lipids and proteins in sheets only a few molecules thick. The lipids, with both water-repelling (hydrophobic) and water-attracting (hydrophilic) regions, form fluid bilayers in water that are selective barriers to polar molecules. Proteins in nature serve distinct functions in membranes as enzymes, receptors, pumps, energy transmitters, or as gates or channels to allow ions and molecules to pass through the membranes. Biomembranes are extremely sensitive to surface conditions, and performance of the membranes is closely related to surface conditions.

Lipid and lipid-protein membranes which mimic biological membranes have been investigated for practical utility. For example, mycelles in which an aqueous solution is encapsulated in an artificial membrane have been used as carriers of drugs, Fendler, J. C&EN Jan. 2, 1984 pp. 25-38, or as vesicles for hemoglobin as an artificial blood substitute.

As a means to investigate the fluid transport characteristics and other properties of lipid-protein membranes, artificial membranes known as black lipid membranes (BLM's) have been prepared across small orifices, Fendler, J., *Membrane Mimetic Chemistry*, John Wiley & Sons, New York 1982. BLM's have had relatively little practical importance because (1) they are notoriously difficult to prepare and (2) they seldom last longer than several hours.

It would be desirable to have stable lipid-protein membranes that would permit their surface sensitivity to be utilized, for example, for the detection of chemical substances.

SUMMARY OF THE INVENTION

In accordance with the present invention, stable lipid-protein membranes are formed across orifices by providing a concentrated aqueous medium containing lipids and proteins. In the presence of air, the medium is applied across an orifice formed in a thin sheet or ticket so that medium fills the orifice with additional medium being carried by the ticket on the periphery of the orifice. As water evaporates reducing the applied volume, medium on the periphery is drawn into the orifice. When all the water is evaporated, a membrane of lipids and protein spans the orifice. A membrane prepared in this manner is stable for an extended period of time and may be stored for a month or longer.

Lipid-protein membranes are found to exhibit at least one altered physical characteristic when chemical substances react with the proteins incorporated in the membrane. Altering characteristics of membranes provides the basis for detection of chemical substances, for example, the electrical resistance of a lipid-protein membrane may change dramatically when the proteins react with an external substance. If the protein is specifically reactive with a particular substance or a particular class of substances, the lipid-protein membrane provides the basis for a specific test for that substance.

IN THE DRAWING

The FIGURE is a diagrammatic representation of a membrane embodying various features of the invention wherein protein molecules are interposed within a bimolecular lipid layer.

DETAILED DESCRIPTION OF THE PREFERRED EMBODIMENTS

In accordance with the present invention, a method is provided for forming lipid-protein membranes across an orifice, with the resulting membranes exhibiting long-term stability, even when stored in air. An orifice is formed in a sheet or ticket of thin material. An aqueous medium containing lipids in excess of saturation and a substantial protein concentration is applied to the orifice in the presence of air (or other non-liquid environment). The medium is applied in excess, filling the orifice and spreading across a surface area of the ticket peripheral to the orifice. As the water evaporates from the applied medium, a stable lipid-protein membrane forms across the orifice.

In accordance with another important aspect of the present invention, the protein which is incorporated in the membrane is selected for its specific reactivity with a chemical substance or a class of chemical substances. Upon reaction of an external substance with protein molecules incorporated within the membrane, characteristics of the membrane are altered and the presence of the substance is evidenced by such a change in membrane characteristics. For example, the electrical resistance of a membrane might change when a substance reacts with membrane proteins, which change in electrical resistance is easily detected by common measuring devices.

Herein the term "lipids" is used to include a substantial proportion of modified lipids, such as phospholipids, having both a polar and a nonpolar domain. With reference to the FIGURE, lipid molecules 10 having a polar domain 12 or end e.g., including phosphate moieties, and a nonpolar end 14 tend to form bimolecular layers in the presence of an aqueous solution. The nonpolar ends 14 of the lipid molecules come together leaving the polar ends exposed to the water on either side. If the aqueous medium includes proteins 20, the protein molecules may become interposed within the bimolecular lipid layer 16 as represented in the FIGURE.

Protein molecules like lipid molecules generally have polar 26 and nonpolar 24 domains, and within a bimolecular lipid layer the nonpolar protein domains 24 align with the interior nonpolar regions of the bimolecular lipid layer while the polar domains tend to extend to the exposed surface or surfaces of the bimolecular lipid layer. Depending upon the arrangement of polar and nonpolar protein domains and the size and configuration of the protein molecule, the protein molecule may protrude from one or both sides of the bimolecular lipid membrane 30. Because proteins are generally adapted to act upon substances in aqueous solution, the active sites of proteins tend to be polar and therefore tend to be exposed when a protein is incorporated in a lipid-protein membrane.

The accepted method of forming lipid or lipid-protein membranes is to prepare an orifice, such as a pinhole, in a sheet or ticket of material, submerge the ticket in an aqueous phase and paint a lipid or lipid-protein preparation across the membrane. Initially, such a membrane appears grey, containing considerable amounts of water in the developing layers. As the developing layers expel water from the regions of the nonpolar lipid domains, the membrane thins irregularly, creating light interference colors. Finally, when the bimolecular lipid layer is fully developed, the membrane turns black, giving rise to the term black lipid membrane (BLM). As noted above, BLM's are difficult to prepare despite the apparent simplicity of the procedure, and the membranes are very unstable.

Surprisingly and unexpectedly, it is found that lipid-protein membranes can be formed from an aqueous lipid and protein-containing medium. in the presence of air and that the membranes that form in this "dry" manner exhibit vastly improved stability relative to membranes prepared in a conventional manner, i.e., submerged in an aqueous solution. The medium is saturated in lipid and also includes emulsified lipid particles. Herein, lipid concentration is understood to refer to the total amount of dissolved and undissolved lipids in the medium.

The protein concentration in the medium is that which is necessary to provide the requisite sensitivity to the membrane that forms. Generally, the protein content (weight per volume) should be at least about 5% by weight of the lipid content. It is found that a protein content equal to at least about 30% by weight of the lipid content tends to stabilize the membranes that are formed; however, the protein content should be no more than about 70 percent of the lipid concentration. Preferably the protein content is between about 45 and about 60 percent by weight of the lipid concentration. The relative proportion of lipid and protein will depend upon the particular lipid source and the particular protein.

It may be desirable in some cases to incorporate more than one type of protein molecule in the membrane. Protein molecules in the membrane, in addition to acting as the external substance-detecting molecules, serve to stabilize the membrane. It may be that a protein molecule which is particularly suitable for detection of a particular substance does not perform a membrane stabilizing function as well as might be desired, in which case it may be desirable to use a mixture of proteins, including an external substance-reactive protein and a relatively inert membrane stabilizing protein. The relative proportions of the proteins in such a protein mixture will depend on the particular application and on such factors as the relative membrane stabilizing ability of the proteins, the reactivity of the active protein for the substance and the degree of membrane characteristic change effected by reaction of the external substance with the active protein. In general, a membrane will incorporate a single, specifically reactive protein; however, in certain situations it may be desirable to incorporate several active proteins. For example, if a membrane is to be used to detect chemical warfare agents, a mixture of proteins, each specifically reactive with a different known chemical warfare agent, might be incorporated into the membrane.

Lipids useful in the invention include any lipid composition with sufficiently distinct polar and nonpolar regions to form a bimolecular membrane. Lecithin is a convenient lipid source, consisting essentially of several hygroscopic phosphatides, particularly phosphatidylcholine. Other lipids useful for forming membranes include, but are not limited to, phosphatidylethanolaminedilauroyl and phosphatidylglyceroldipalmitoyl. The lipids may contain a minor proportion of lipids not having distinct polar and non-polar regions, such as cholesterol; however, for efficient production of stable membranes, it is considered necessary that the lipid molecules having distinct polar and non-polar ends comprise at least about 70% by weight of the lipid component. This may vary, however, depending upon the species and content of the protein.

The protein is selected according to the chemical substance which is to be detected. Antibodies are protein molecules that react specifically with antigens or portions of antigens, such as haptens, against which the antibodies are raised, and antibody molecules may be incorporated in lipid-protein membranes for detection of specific antigens. Enzymes are protein molecules exhibiting strong affinity for particular substrates.

If protein molecules are not available that will specifically react with a particular substance, they may be produced. Using the antibody approach, antibodies can be raised against a wide variety of substances. If the chemical substance is too small to induce antibody production in a host-animal, it may be conjugated to a carrier protein and the conjugate protein used to induce antibody. Alternatively, a moiety reactive with a substance to be detected may be covalently linked to a protein molecule and the moiety-protein conjugate incorporated in the membrane.

In addition to the lipids and proteins, the medium may contain other substances, including ions. Ions, particularly metal ions, are found to have a significant impact on the membrane which eventually forms; however, a good deal remains to be studied regarding the effects that ion incorporation in the medium has on the membrane that is eventually formed. The ions that are in the medium are not necessarily incorporated into the membrane but may affect the manner e.g., orientation, in which the protein molecules are incorporated into the membrane.

The medium may also contain other organic substances such as polysaccharides and chondroitin sulphate. Incorporation of such additional organic substances will effect the characteristics of the membranes that are formed. By using additional substances, a membrane may be given certain physical properties, such as controlled porosity, suitable for a particular application. The amount of additional organic substances that can be successfully incorporated into a membrane depends upon a number of factors, such as the polarity of the substance. The additional organic substance or substances in the medium may comprise up to about 30% by weight of the lipid, resulting in a membrane with a generally corresponding weight percentage of additional organic substance.

The ticket material can be chosen from a variety of substances, depending upon how the ticket is to be used. The ticket material should be a sheet of relatively thin material, e.g., between about 0.3 and about 1.5 mm thick. The ticket may be formed, of a metal, but preferably is formed of a suitable polymer, such as polystyrene. If the ticket is to be exposed to a solution for an extended period of time, it is preferred that the material be nonreactive with the solution. If the membrane is used to detect a substance according to electrical resistance of the membrane, the ticket is formed of a dielectric material. Such a dielectric material may be coated with a conducting material on both surfaces as electrode means for applying an electrical potential across the membrane.

Membrane construction begins with preparation of the medium comprising an emulsion of lipids with dissolved proteins. Lipid is added into an aqueous medium to provide a final lipid concentration of between about 2 and about 25 gm per liter of medium. The lipid is emulsified by standard emulsification techniques, such as rapid mixing, sonification, release under pressure through a constricted orifice, etc. In the emulsified medium, the aqueous phase is saturated with dissolved lipids, and the undissolved lipids exist as tiny lipid particles or as tiny vesicles known as liposomes. The protein may be added to the aqueous medium along with the lipid component prior to emulsification or added subsequent to emulsification of the lipid component. It is found that the most stable membranes result when the solution is used fresh.

Orifices are appropriately formed in the ticket, e.g., by drilling, stamping, etc. For purposes of this invention, the orifices are generally between about 0.25 and about 3 mm in diameter, 0.5 to 1.5 mm being a preferred size range. Even larger membranes may be desirable in some instances; however, membranes become increasingly difficult to prepare as the diameter increases and may be less stable once prepared. Preferably, the orifices are round, but they may take other shapes.

The medium is applied to the membrane in a manner so that it fills the orifice and so that there is sufficient lipid and protein in the region of the orifice to complete a membrane comprising a bimolecular lipid membrane with interspersed protein moieties. A difficulty in applying medium to the orifices is that surface tension tends to keep the medium out of the orifice. Accordingly, care must be taken in application of the medium to the ticket to assure that the medium is forced into the orifice. A convenient means of applying the medium is with a fibrous material, e.g., cotton swabs. The swab forces medium into the orifices and leaves a peripheral smear of medium on the surface of the ticket to provide the excess medium necessary to assure a sufficient supply of lipids and protein to form the membrane across the orifice. The exact amount of medium that must be applied into and peripheral to the orifice depends upon the size of the orifice and the concentration of the lipids and proteins in the medium. However, generally, particular attention need not be paid to the amount of medium applied because a reasonable excess application of medium does not adversely affect the formation of the membrane which is controlled largely by the polar-nonpolar interactions to produce a bimolecular lipid layer with interspersed proteins.

The membrane forms as the water evaporates from the medium. The amount of medium within the orifice itself is generally insufficient to supply the requisite lipids and proteins, and as the medium dries, surface tension acts to draw medium lying about the periphery of the orifice into the orifice to provide the additional lipids and proteins needed to form the membrane.

Membranes that are formed "dry", i.e., in air, exhibit amazing stability relative to membranes formed across orifices of tickets that are submerged in water or an aqueous medium. Whereas a typical membrane formed under water has a life of about 2 hours, and almost never more than 24 hours, membranes formed in air according to the invention will typically last for a month, and membranes which exist for several months are common.

The reason for the increased stability of membranes produced by the dry method is not fully understood, and applicant is not bound by any particular theory of why the stability is achieved. However, it is believed that when membranes are formed by the dry method, improved incorporation of proteins into the membrane is effected and that the membrane composition more closely reflects the relative contents of lipid and protein in the medium. When a membrane is formed under water there may be a tendency to leach protein molecules from the lipid-protein composition and for the water to affect the manner in which the proteins are incorporated into the bimolecular lipid layer. This problem is generally avoided when the membrane forms during evaporation to dryness of a small amount of medium in air.

The term "air" is used herein to denote a gaseous rather than a liquid environment, and is not limited to a natural air atmosphere. It is felt that components of the air itself do not interact with the lipids or proteins but rather the air merely serves to promote evaporation of water. Any gas that is substantially inert to the lipids and protein would serve the same function; however, there are no known benefits in providing special atmospheres. Preferably the relative humidity of the atmosphere is maintained below about 30% to hasten the membrane-forming process.

Typically, formation of the membrane through evaporation to dryness will take between about 6 and about 16 hours, depending upon a number of factors, including temperature and humidity of the air, initial water content in the medium, size of the orifice and amount of medium applied. Air drying at room temperature and below 30% relative humidity for 24 hours generally assures evaporation to dryness.

After formation of the membrane, the ticket may be stored in air or in solution for extended periods of time. Storage in air is preferred except for use in a system in which it is required that the membrane be in continuous contact with a solution.

The invention will now be described in greater detail by way of specific examples.

EXAMPLE 1

In sheets of polystyrene 0.68 mm thick, a number of orifices are stamped of 0.28, 0.57 and 0.85 mm diameter sizes. Knox brand gelatin is dissolved in distilled water. To various gelatin solutions are added various amounts of egg white lecithin obtained from a grocery store. In each case the lecithin is emulsified with the solution by vigorous stirring. The polystyrene sheets are placed horizontally and various media are applied into and peripheral to the orifices using cotton swabs. The applications are allowed to evaporate to dryness in air at 25° and 30% relative humidity for 24 hours. The membrane-forming capabilities of the various media are represented in the following table in which concentrations of gelatin and lecithin are expressed as mg/ml of the total emulsion:

TABLE

| No. | lipid conc. (g/l) | gelatin conc. (g/l) | orifice diam. (mm) | membrane formation (+ or −) | membrane duration (days) |
|---|---|---|---|---|---|
| 1 | 6.8 | 2.0 | 0.66 | + | 100 |
| 2 | 11.6 | 4.3 | 0.33 | + | 120 |
| 3 | 11.6 | 4.3 | 1.0 | + | 100 |
| 4 | 2.0 | 6.8 | 1.0 | + | 60 |
| 5 | 3.2 | 5.4 | 1.5 | + | 7 |

The results indicate that membranes can be formed relatively easily according to the method of the invention using emulsions of a wide range of lipid and protein concentrations and that the membranes formed by this method are amazingly stable as compared to the prior art underwater method of BLM formation.

EXAMPLE 2

An emulsion of lecithin is prepared by vigorously stirring 19.5 mg in 4 ml of water. To this is added 0.6 ml of an aqueous solution containing 55 grams of gelatin per ml and 1.2 ml of an aqueous solution containing 1 mg of rabbit antibody to human serum albumin per ml (obtained from Calbiochem-Behring). The final concentrations were 3.4 mg lecithin/ml, 5.7 mg gelatin/ml and 0.2 mg antibody/ml. A 0.68 mm thick polystyrene sheet is coated on each side with copper to a thickness of about 50μm to form a test ticket. Orifices of 0.57 and 0.85 mm diameters are stamped into the tickets. Emulsion is swabbed into and around the orifices. The tickets are dried in air for 24 hours at 25° C., 30% relative humidity. The 57 mm orifices, exhibit considerable copper corrosion. The 0.85 mm orifices exhibit relatively little copper corrosion.

Leads from an ohm meter are attached to the opposed surfaces of a dry ticket. The measured resistance of the dry tickets is very high, e.g., in the range of above 2 megaohms.

A ticket with a 0.57 mm orifice is held horizontally and a drop of water (approximately 0.05 ml) is applied to one side of the 0.57 mm membrane. The ticket is turned over, surface tension holding the drop suspended from the bottom side of the ticket, and a drop of water is applied to the top side of the membrane. The resistance stabilizes at 300,000 ohms. 50 μl of a 0.15 molar saline solution is added to the drop of water on the top side of the membrane, but no appreciable resistance change is detected. 50 micrograms of human serum albumin is then added to the drop on the top side of the membrane. The resistance rises to 600,000 ohms in 15 sec., indicating a permeability change in the membrane.

To a first 0.85 mm membrane is added a drop of water (about 0.05 ml) on each side. The resistance stabilizes at 300,000 ohms. The addition of 50 μl of 0.15 molar saline to the drop on the top side does not appreciably change the resistance; however, the addition of 50 μg of human serum albumin drops the resistance to 120,000 ohm within 5 seconds.

The experiment is repeated with a second 0.85 mm membrane with similar results except that the resistance drops from 70 ohms to 55 ohms.

The above results show that lipid-protein membranes undergo substantial changes when a foreign substance reacts with the proteins incorporated therein, and that such membranes can therefore be used to test for the presence of a foreign substance. Advantageously, the presence of a particular foreign substance is very quick and in some cases almost instantaneously.

The results of the above experiment are somewhat varied due to the effects of varying concentrations of metal ions in the membranes and/or in solution, and it will be necessary to eliminate or control factors to provide more reproducible and predictable tests. This may be accomplished for example by using a less corrosive electrode material, such as silver, gold or platinum.

EXAMPLE 3

A solution is prepared as in example 2, except that is contains 5.5 mg lecithin/ml, 5.6 mg gelatin/ml, and 0.2 mg antibody/ml (the antibody being toward human serum albumin). The solution is swabbed into a 1 mm diameter hole in a gold-coated polystyrene ticket.

A hanging drop of water is placed on the bottom of the membrane after it had dried 24 hours, and a drop of aqueous solution containing 25 micrograms of bovine serum albumin is placed on top of the membrane. The resistance equilibrates at 140,000 ohms. The drop of BSA is replaced with a drop of aqueous soulution containing 50 micrograms of human serum albumin (HSA), and the resistance equilibrates at over 200,000 ohms.

It is found that the resistance always increases when the lecithin, gelatin, anti-HSA membrane is prepared across 1 to 1.5 mm holes in gold-coated polystyrene tickets when an HSA solution is added after other solutions in a typical experiment.

This example shows that the membrane differentiates between BSA and HSA. That is, the BSA does not cause a rise in resistance as does the HSA.

In this experiment it is also demonstrated that a gold coated ticket is superior to a copper coated ticket because it does not oxidize. Thus while with a copper coated ticket there is poor control of ion concentration, a gold ticket permits good control of ion concentration.

It may now be more fully appreciated that the invention provides black lipid membranes that are much more stable than those described in the prior art. The membranes are very sensitive to agents that react with the incorporated proteins providing almost instantaneous indication of the presence of such foreign substances. Because proteins, such as antibodies or enzymes, may have very specific activity, the test membranes according to the invention, in addition to being very sensitive, may be very specific to a particular foreign substance or class of substance.

While the invention has been described in terms of certain preferred embodiments, modifications obvious to one with ordinary skill in the art may be made without departing from the scope of the present invention. For example, electrical conductivity is only one membrane parameter affected by reaction of incorporated proteins with foreign substances, and other means of detection may be used to measure protein-foreign substances reaction according to different membrane parameters.

Various features of the invention are set forth in the following claims.

What is claimed is:

1. A process of preparing lipid-protein membranes comprising, providing a sheet of material, forming an orifice in said sheet up to about 3 mm in diameter, preparing an aqueous medium containing between about 2 and about 25 mg/ml of dissolved and emulsified lipid and between about 1 to about 10 mg/ml of a protein, said protein equaling between about 5 and about 70 percent by weight of said lipid material, with said sheet exposed to air, applying said medium to said orifice in an effective amount for filling said orifice having protein molecules interspersed as integral membrane proteins and providing sufficient lipid and protein to form a biomolecular lipid layer across said orifice, and evaporating the water in said medium in the presence of air to provide a stable lipid-protein membrane.

2. A membrane produced by the process of claim 1.

3. A process according to claim 1 wherein said sheet is between about 0.3 and about 1.5 mm. thick, said medium is applied into said orifice to overfill the same, whereby as water evaporates from said applied medium, medium peripheral to said orifice fills said orifice.

4. A process in accordance with claim 1 wherein said protein is specifically reactive with a chemical substance or a limited class of chemical substances.

5. A process according to claim 1 wherein said medium is prepared with additional nonlipid organic molecules up to about 30% by weight of said lipid, said additional molecules altering physical characteristics of the membrane that is formed.

6. A process according to claim 1 wherein said protein comprises between about 45 and about 60 percent by weight of said lipid in said solution or emulsion.

7. A membrane produced by the process of claim 6.

8. A method according to claim 1 wherein said protein is an antibody.

9. A membrane produced by the process of claim 8.

10. A method according to claim 1 wherein said protein is an enzyme.

11. A membrane produced by the process of claim 10.

12. A process according to claim 1 wherein said medium is applied to said sheet using a fibrous swab.

13. A membrane produced by the process of claim 12.

14. A method of detecting the presence of a substance comprising:

providing a membrane which is formed by a process of preparing an aqueous medium containing between about 2 and about 25 mg/ml of dissolved and emulsified lipid and between about 1 and about 10 mg/ml of a protein, said protein equaling between about 5 and about 70 percent by weight of said lipid and a substantial portion of the protein being reactive with the substance to be detected, applying said medium to an orifice with a diameter up to 3 mm in a sheet of material with said sheet exposed to air, the medium being applied in an effective amount for filling said orifice and providing sufficient lipid and protein to form a biomolecular lipid layer across said orifice having protein molecules interspersed as integral membrane proteins, and evaporating the water in said medium in the presence of air to provide a membrane;

exposing the membrane to material potentially containing said substance, and detecting a change in a physical characteristic of said membrane.

15. A method according to claim 14 wherein a change in the electrical resistivity of said membrane is detected.

16. A method according to claim 14 wherein said protein is an antibody.

17. A method according to claim 14 wherein said protein is an enzyme.

18. A method according to claim 14, wherein said protein comprises between about 45 and about 60 percent by weight of said lipid.

19. A method according to claim 14 wherein said membrane is exposed to an aqueous solution potentially containing said substance.

20. A method according to claim 14 wherein said membrane also includes additional nonlipid organic molecules up to about 30% by weight of said lipid to alter the physical charcteristics of the membrane.

* * * * *

UNITED STATES PATENT AND TRADEMARK OFFICE
CERTIFICATE OF CORRECTION

PATENT NO. : 4,661,442
DATED : APRIL 28, 1987
INVENTOR(S): HERBERT R. LUKENS

It is certified that error appears in the above-identified patent and that said Letters Patent is hereby corrected as shown below:

FACE, PUBLICATIONS, within "Y. Roven" Publication, line 3, change "35254s" to --353545--.

Column 1, lines 51 & 52, delete spacing for new paragraph after "small" and before "orifice".

Column 3, line 2, change "domains" to --regions--.

Column 3, line 30, delete "." (period) after "medium".

Column 4, line 18, replace "non-polar" with --nonpolar--.

Column 4, line 22, replace "non-polar" with --nonpolar--.

Column 7, line 66, change "The-experiment" to --The experiment--.

Column 8, line 7, change "instantaneously" to --instantaneous--.

Column 8, line 17, change "is" second occurrence to --it--.

Column 8, line 27, change "soulution" to --solution--.

Column 8, lines 38 & 39, change "gold coated" to "gold-coated--.

Column 8, line 39, change "copper coated" to --copper-coated--.

Column 8, lines 40 & 41, change "copper coated" to --copper-coated--.

UNITED STATES PATENT AND TRADEMARK OFFICE
CERTIFICATE OF CORRECTION

PATENT NO. : 4,661,442

DATED : APRIL 28, 1987

INVENTOR(S) : HERBERT R. LUKENS

It is certified that error appears in the above-identified patent and that said Letters Patent is hereby corrected as shown below:

Column 9, lines 13 & 14, delete "having protein molecules interspersed as integral membrane proteins" and at Column 9, line 16, after "orifice" insert --having protein molecules interspersed as integral membrane proteins--.

Column 9, Claim 3, line 21, delete "." (period) after "mm".

Column 10, Claim 20, line 43, change "charcteristics" to --characteristics--.

Signed and Sealed this

Twenty-ninth Day of September, 1987

Attest:

DONALD J. QUIGG

*Attesting Officer*　　*Commissioner of Patents and Trademarks*